(12) United States Patent
Sandusky

(10) Patent No.: US 6,750,968 B2
(45) Date of Patent: Jun. 15, 2004

(54) DIFFERENTIAL NUMERICAL APERTURE METHODS AND DEVICE

(75) Inventor: John V. Sandusky, Albuquerque, NM (US)

(73) Assignee: Accent Optical Technologies, Inc., Bend, OR (US)

( * ) Notice: Subject to any disclaimer, the term of this patent is extended or adjusted under 35 U.S.C. 154(b) by 169 days.

(21) Appl. No.: 09/969,939

(22) Filed: Oct. 2, 2001

(65) Prior Publication Data

US 2002/0039184 A1 Apr. 4, 2002

Related U.S. Application Data

(60) Provisional application No. 60/237,950, filed on Oct. 3, 2000.

(51) Int. Cl.[7] .............................. G01J 4/00; G01N 21/55
(52) U.S. Cl. ........................................ 356/369; 356/445
(58) Field of Search ................................ 356/369, 445, 356/446, 448

(56) References Cited

U.S. PATENT DOCUMENTS

| | | | |
|---|---|---|---|
| 3,814,943 A | | 6/1974 | Baker et al. |
| 3,927,253 A | | 12/1975 | Jungles et al. |
| 4,710,642 A | | 12/1987 | McNeil |
| 4,931,830 A | | 6/1990 | Suwa et al. |
| 5,164,790 A | | 11/1992 | McNeil et al. |
| 5,166,752 A | | 11/1992 | Spanier et al. |
| 5,218,415 A | * | 6/1993 | Kawashima ............. 356/139.1 |
| 5,241,369 A | | 8/1993 | McNeil et al. |
| 5,561,525 A | | 10/1996 | Toyonaga et al. |
| 5,596,411 A | | 1/1997 | Fanton et al. |
| 5,638,353 A | | 6/1997 | Takahashi |
| 5,703,692 A | | 12/1997 | McNeil et al. |
| 5,798,837 A | | 8/1998 | Aspnes et al. |
| 5,867,276 A | | 2/1999 | McNeil et al. |
| 5,877,859 A | | 3/1999 | Aspnes et al. |
| 5,880,838 A | * | 3/1999 | Marx et al. ................. 356/498 |
| 5,889,593 A | | 3/1999 | Bareket |
| 5,910,842 A | | 6/1999 | Piwonka-Corle et al. |
| 5,912,741 A | | 6/1999 | Carter et al. |
| 5,955,739 A | | 9/1999 | Kawashima |
| 6,034,776 A | | 3/2000 | Germer et al. |
| 6,037,579 A | | 3/2000 | Chan et al. |
| 6,052,188 A | | 4/2000 | Fluckiger et al. |
| 6,100,985 A | | 8/2000 | Scheiner et al. |
| 6,122,046 A | * | 9/2000 | Almogy .................... 356/237.2 |
| 6,130,750 A | | 10/2000 | Ausschnitt et al. |
| 6,134,012 A | | 10/2000 | Aspnes et al. |
| 6,281,974 B1 | * | 8/2001 | Scheiner et al. .............. 356/491 |
| 2003/0025909 A1 | * | 2/2003 | Hallstadius ................. 356/436 |

\* cited by examiner

Primary Examiner—Rodney Fuller
(74) Attorney, Agent, or Firm—Stephen A. Slusher

(57) ABSTRACT

Devices and methods for differential numerical aperture analysis of samples, utilizing angle-of-incidence measurements resulting from variable illumination or observation numerical apertures, or both. Metrology applications are provided, and more particularly including scatterometer, ellipsometer and similar analysis methods, including bi-directional reflectance or transmission distribution function measurement. The provided devices and methods enable analysis of critical dimensions of samples utilizing a minimum of moving parts, with the range of striking or scattering angles varied by a variable numerical aperture or apertures.

41 Claims, 10 Drawing Sheets

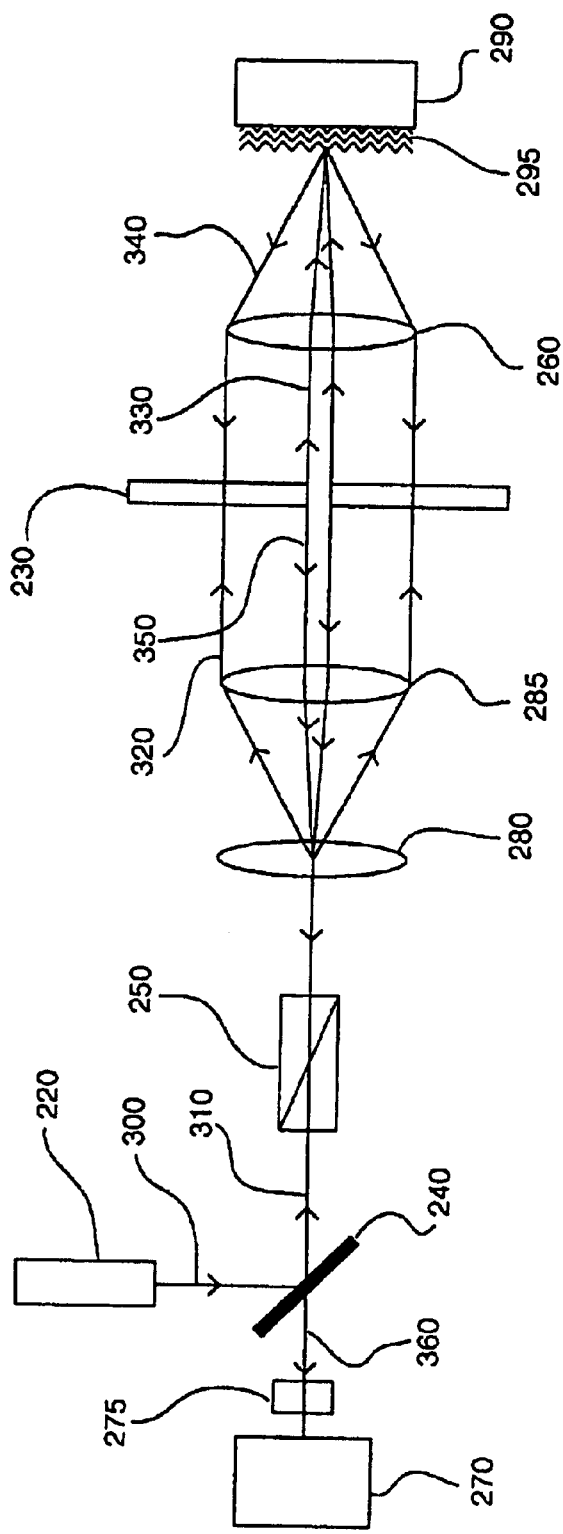
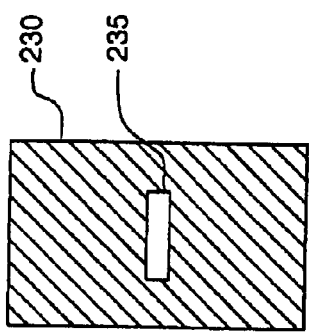
FIG. 8A
FIG. 8B

DIFFERENTIAL NUMERICAL APERTURE METHODS AND DEVICE

CROSS-REFERENCE TO RELATED APPLICATIONS

This application claims the benefit of the filing of U.S. Provisional Patent Application Ser. No. 60/237,950, entitled Differential Numerical-Aperture Methods and Device, filed on Oct. 3, 2000, and the specification thereof is incorporated herein by reference.

BACKGROUND OF THE INVENTION

1. Field of the Invention (Technical Field)

The present invention relates to metrology, and more particularly to scatterometer, ellipsometer and similar analysis methods utilizing angle-of-incidence measurements, and yet more particularly to an apparatus and method that utilizes differentially changing the illumination and observation numerical apertures and determinations based thereupon.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A variety of scatterometer and related devices and measurements have been used for characterizing the microstructure of microelectronic and optoelectronic semiconductor materials, computer hard disks, optical disks, finely polished optical components, and other materials having lateral dimensions in the range of tens of microns to less than one-tenth micron. For example, the CDS200 Scatterometer, made and sold by Accent Optical Technologies, Inc. is a fully automated nondestructive critical dimension (CD) measurement and cross-section profile analysis system, partially disclosed in U.S. Pat. No. 5,703,692. This device measures the specular reflection of a sample as a function of angle-of-incidence and polarization by scanning a laser beam laterally across the entrance pupil of a high numerical aperture lens system. This device can repeatably resolve critical dimensions of less than 1 nm while simultaneously determining the cross-sectional profile and performing a layer thickness assessment. This device monitors the intensity of a single diffraction order as a function of the angle of incidence of the illuminating light beam. The intensity variation of the $0^{th}$ or specular order as well as higher diffraction orders from the sample can be monitored in this manner, and this provides information that is useful for determining the properties of the sample target which is illuminated. Because the process used to fabricate the sample target determines the properties of a sample target, the information is also useful as an indirect monitor of the process. This methodology is described in the literature of semiconductor processing. A number of methods and devices for scatterometer analysis are taught, including those set forth in U.S. Pat. Nos. 4,710,642, 5,164,790, 5,241,369, 5,703,692, 5,867,276, 5,889,593, 5,912,741, and 6,100,985.

Scatterometers and related devices can employ a variety of different methods of operation. In one method, a single, known wavelength source is used, and the incident angle $\Theta$ is varied over a determined continuous range. In another method, a number of laser beam sources are employed, optionally each at a different incident angle $\Theta$. In yet another method, an incident broad spectral light source is used, with the incident light illuminated from some range of wavelengths and the incident angle $\Theta$ optionally held constant. Variable phase light components are also known, utilizing optics and filters to produce a range of incident phases, with a detector for detecting the resulting diffracted phase. It is also possible to employ variable polarization state light components, utilizing optics and filters to vary the light polarization from the S to P components. It is also possible to adjust the incident angle over a range $\Phi$, such that the light or other radiation source rotates about the target area, or alternatively the target is rotated relative to the light or other radiation source. Utilizing any of these various devices, and combinations or permutations thereof, it is possible and known to obtain a diffraction signature for a sample target.

Besides scatterometer devices, there are other devices and methods capable of determining the diffraction signatures at the $0^{th}$ order or higher diffraction orders using a light-based source that can be reflected off of or transmitted through a target sample, such as a diffraction grating, with the light captured by a detector. These other devices and methods include ellipsometers and reflectometers, in addition to scatterometers.

A number of methods of determining CD utilizing various techniques and devices are disclosed in the prior art. Thus U.S. Pat. No. 5,910,842, to Piwonka-Corle et al., discloses a method and system for spectroscopic ellipsometry employing reflective optics over a range of incident angles. This discloses an actuator-positioned plate with an aperture therein, to observe incidence angles in a selected narrow range. However, this patent does not disclose opening the aperture differentially to integrate a wider range of incident angles.

U.S. Pat. No. 5,877,859, to Aspnes and Opsal, and related U.S. Pat. No. 5,596,411 to Fanton and Opsal, disclose an ellipsometer and method of ellipsometry. Use of an aperture in certain embodiments is disclosed, but only to control the size of the field of the sample that is ultimately imaged on a detector array. In a related approach, an angle-integrated ellipsometer is also provided, but at a fixed range of angles over a large range of wavelengths.

U.S. Pat. No. 5,166,752, to Spanier et al., discloses an ellipsometer and method of ellipsometry. This provides a variable aperture, but does not disclose varying the aperture during a measurement cycle, and further involves separate simultaneous detection of a plurality of different angles of incident light.

One method employed for determination of CD is by measurement of what is called the BRDF (Bi-directional Reflectance Distribution Function). In this method, the BRDF is the fraction of a light beam of wavelength $\lambda$ and polarization state described by Stokes vector $S_0$ incident on a scattering surface at azimuth angle $\phi_0$ and zenith angle $\Theta_0$, scattered into a differential solid angle $\delta\Omega$ centered at the azimuth angle $\phi$ and zenith angle $\Theta$ with polarization state described by Stokes vector S. The BRDF for most surfaces is a complicated function of the incident angle and Stokes vector of the incident photon, the scattering direction, and the surface properties. An ideal mirror, by contrast, has the simplest BRDF: it is unity when the scattered zenith angle is equal to the incident zenith angle and the scattered azimuth angle is opposite the incident azimuth angle, zero for all other scattering angles, and the scattered polarization state is equal to the incident polarization state.

Many surfaces have symmetry properties that reduce the number of independent measurements necessary to describe its BRDF. For example, a diffraction grating of infinite lateral dimensions constructed from dielectric materials does not rotate or mix the polarization state of light incident orthogonal to the grating grooves. The dependence of the BRDF on incident polarization state at this orthogonal orientation is described simply as two independent BRDFs representing the S and P incident polarization states. Under these conditions the BRDF is also symmetric under grating azimuth rotations of 180 degrees. It is typical for commercial scatterometers to take advantage of these symmetries to simplify the BRDF model and the measurement apparatus.

The BRDF is a broadly applicable definition for the quantification of surface scattering, and is most often applied to optically rough surfaces that scatter light broadly into many directions. By contrast, most common optical surfaces do not scatter light broadly; they are optically smooth and have simple mirror-like BRDFs. Such surfaces are typically described by reflectance, diffraction efficiency, or polarization rotation, rather than by stating their full BRDF. These surface properties are, however, special cases of the more general BRDF.

Opaque optical surfaces are well described by their BRDF. However, description of translucent optical surfaces may additionally require description of the Bi-Directional Transmission Distribution Function (BTDF), which is defined for transmission measurements analogously to the BRDF. The BRDF and BTDF are themselves subsets of the Bi-Directional Scattering Distribution Function (BSDF) which describes surface scattering under the most general conditions.

In the semiconductor industry, integrated processing and manufacturing devices are being constructed, incorporating various stepper or exposure components, developing components, baking components, metrology components and the like. Thus a standard silicon wafer of any conventional size is introduced into the integrated processing and manufacturing device, and all fabricating and metrology steps take place within the device, generally under computer control, with a finished wafer, with desired structures etched thereon, exiting the device. This approach preferably requires integrated metrology, such as measurement of CD. It is thus desirable that these components be miniaturized to the extent possible, and occupy the smallest possible footprint, and further have a minimum of moving parts.

SUMMARY OF THE INVENTION
(DISCLOSURE OF THE INVENTION)

In one embodiment, the invention provides an apparatus for determining parameters of a sample, the apparatus including a source for generating a beam of light; a variable illumination numerical aperture component, variable over a numerical aperture range while obtaining data for determining parameters, the varying numerical aperture thereby varying the range of angles at which illuminating rays strike the sample; a variable observation numerical aperture component, variable over a numerical aperture range while obtaining data for determining parameters, the varying numerical aperture thereby varying the range of angles at which scattered rays from the sample are accepted; and a first detection system positioned to receive and characterize the light accepted by the variable observation numerical aperture component. The apparatus can further include a beam splitter positioned to direct the beam of light generated by the source to the sample, and may further include a lens system positioned such that the lens system focuses the illuminating rays striking the sample and collects scattered rays from the sample. In a related embodiment, the apparatus includes a first component for polarizing light positioned such that the component polarizes light striking the sample; and a second component for polarizing light positioned such that the component polarizes light scattered from the sample prior to receipt and characterization by the first detection system. The first and second components for polarizing light can include a polarizer, wave plate, electrooptic modulator, photoelastic modulator, liquid crystal or any polarization rotation device. The apparatus can also include a second detection system positioned to receive and characterize a first portion of the light subsequent to the variable illumination numerical aperture but prior to striking the sample, such detection system also optionally containing components for polarized light detection. A beam splitter may be positioned to direct the first portion of the light to the second detection system and a second portion of the light to the sample. In the apparatus, the variable illumination numerical aperture can include an iris, a zoom lens assembly, a variable beam expander, a variable aperture stop magnification imaging assembly, a spatial Fourier transform of the aperture stop assembly or a combination of the foregoing. The variable aperture stop magnification imaging assembly can include an assembly providing a projected image. The iris may include a non-mechanical iris, including but not limited to a liquid crystal array forming an iris. The iris may be of any shape. In the apparatus, the first detection system may be a photodetector or a spectrometer. The first detection system may also include a computer-compatible output for recording data relating to receipt and characterization of light, and may further include a processor for controlling the numerical aperture of the variable illumination numerical aperture component and the aperture of the variable observation numerical aperture component. In the apparatus, the numerical aperture of the variable illumination numerical aperture component may be variable over a numerical aperture range from 0 to about 1. Similarly, the numerical aperture of the variable observation numerical aperture component may be variable over a numerical aperture range from 0 to about 1.

In a related embodiment, the apparatus may include a source for generating a beam of light; a variable illumination numerical aperture component for varying the numerical aperture over a numerical aperture range while obtaining data for determining parameters, thereby varying the range of angles at which illuminating rays strike the sample; an observation aperture component, accepting scattered rays from the sample at a fixed range of angles; and a first detection system positioned to receive and characterize the light accepted by the observation aperture component.

In another related embodiment, the apparatus may include a source for generating a beam of light; an illumination aperture component, determining the range of angles at which illuminating rays strike the sample; and a variable observation numerical aperture component for varying the numerical aperture over an incremental numerical aperture range while obtaining data for determining parameters, thereby varying the range of angles at which scattered rays from the sample are accepted; and a first detection system positioned to receive and characterize the light accepted by the variable observation aperture component.

The invention further provides a method for determining parameters of a sample, the method comprising the steps of generating a beam of light; focusing the beam of light on the sample; varying at least one parameter selected from the group consisting of the range of angles of incidence of the beam of light to the sample and the range of angles of detected scatter from the sample by means of at least one variable numerical aperture; and detecting and characterizing the scattered light. In the method, the step of varying at least one parameter can include varying both the range of angles of incidence of the beam of light to the sample and the range of angles of detected scatter from the sample. The range of angles of incidence of the beam of light to the sample can be varied by means of a first variable numerical aperture and the range of angles of detected scatter from the sample can be varied by means of a second variable numerical aperture. The method can further include the steps of polarizing the light striking the sample and polarizing the light scattered from the sample. In the method, the at least one variable numerical aperture can include an iris, a zoom lens assembly, a variable beam expander, a variable aperture stop magnification imaging assembly, a spatial Fourier transform of the aperture stop assembly or a combination of the foregoing. Detecting and characterizing can include use of a photodetector or a spectrometer, and can further include a computer-compatible output for recording data relating to receipt and characterization of light.

A primary object of the present invention is to provide a method and device for CD measurement of structures, and in particular regular structures, by means of a differential numerical aperture technique.

Another object of the present invention is to provide a method and device for scatterometry or ellipsometry analysis wherein the range of incident angles is varied by means of a variable numerical aperture component.

Another object of the present invention is to provide a method of differential numerical aperture analysis of CD of structures, wherein an illumination system is employed which varies by small and differential increments the range of angles at which illuminating rays strike the structure surface, thereby providing a variable illumination numerical aperture, or wherein an observation system is employed which varies by small and differential increments the range of angles at which light scattered from the structure are accepted, thereby providing a variable observation numerical aperture, or wherein both such illumination system and observation system are employed.

Another object of the present invention is to provide a method and device for differentially changing the illumination numerical aperture or the observation numerical aperture, or both, while recording the power scattered into the observation numerical aperture.

Another object of the present invention is to provide a method and device utilizing observations related to a variable illumination numerical aperture or a variable observation numerical aperture, or both, to find unknown parameters in a model describing scattering from a structure surface, in part by integrating the scattering model over the illumination and observation numerical apertures.

A primary advantage of the present invention is that it provides a device for scatterometry or ellipsometry with a minimum of moving parts, and occupying a very small footprint.

Another advantage of the present invention is that it provides a device for CD determination that may be incorporated as a module or component in an integrated semiconductor processing and manufacturing device.

Another advantage of the present invention is that it provides a method for CD metrology which may be applied to either scatterometry or elipsometry techniques, or in general to any method employing BRDF, BTDF or BSDF analysis.

Yet another advantage of the present invention is that it provides a method for scanning through a variety of incident or reflective angles, or both, by varying the numerical aperture in variable numerical aperture components.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 8 is a schematic diagram of an embodiment of the invention, wherein a single polarizer and single variable numerical aperture, utilizing a variable slit iris, is employed for both illumination and observation;

DESCRIPTION OF THE PREFERRED EMBODIMENTS

Best Modes for Carrying Out the Invention

Figure 1:
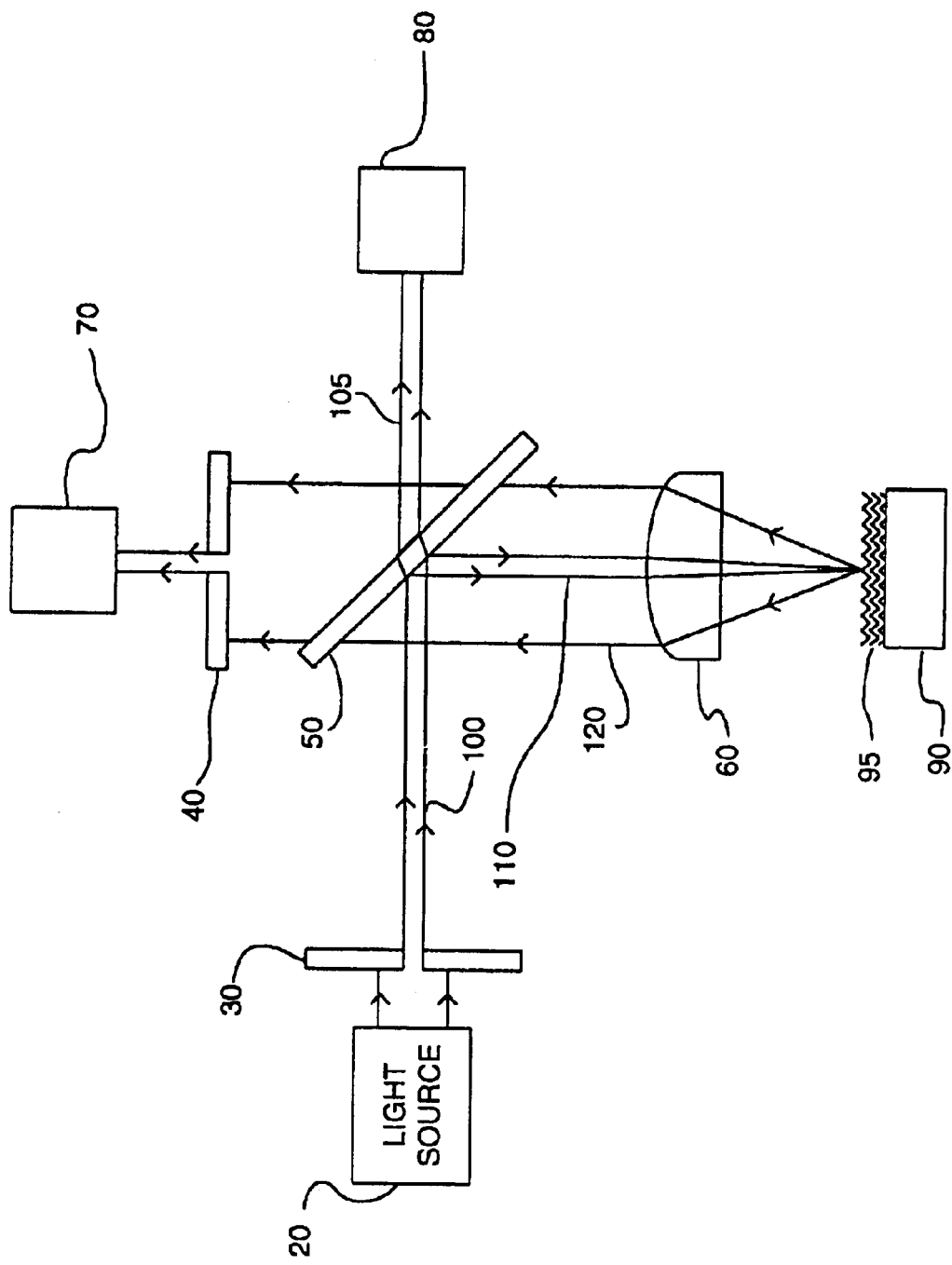
FIG. 1 is a schematic diagram illustrating an embodiment of the invention wherein both a variable illumination and observation numerical aperture is provided by means of a variable iris.
Figure 10A:
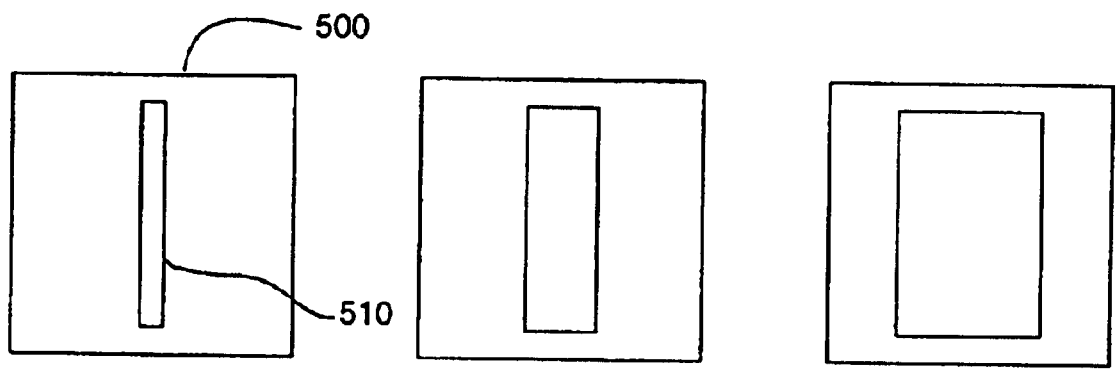
Figure 10B:
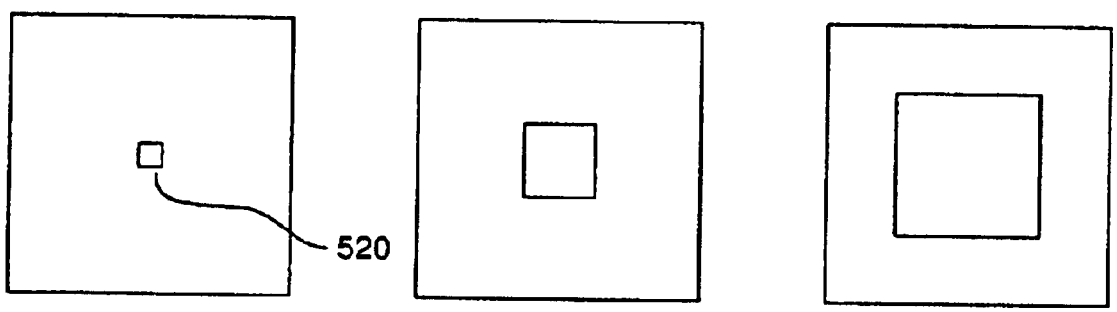
Figure 10C:
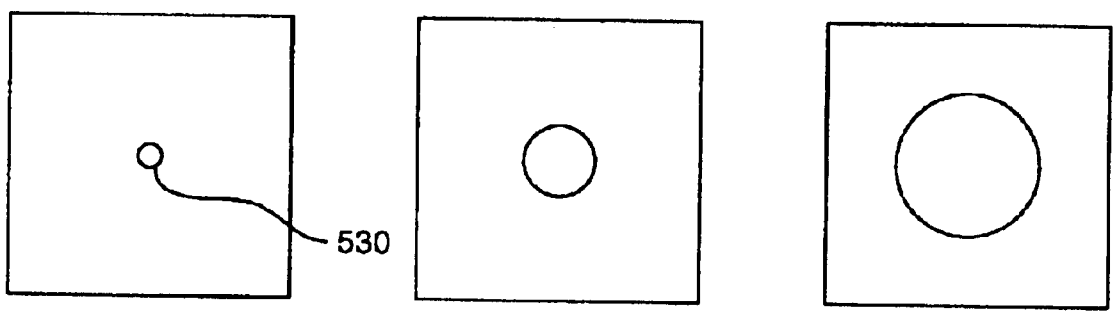

A generalized embodiment of a device of the invention is provided in FIG. 1. Light source 20 provides a source of light for illuminating beam 100, which light source 20 may produce any form of light, either within or without the visible spectrum. Light source 20 conventionally produces monochromatic light, and preferably coherent light, and thus conventional lasers, light-emitting diodes and the like may be employed. However, in embodiments of the invention, as hereafter described, other light sources and forms of light may be employed. The column of illuminating beam produced by light source 20 is partially passed through illumination aperture 30, which illumination aperture 30 may be varied during the process of measurement or scan as to size or shape, or both. In one embodiment, illumination aperture 30 includes an iris, such as depicted in FIG. 10. In FIG. 10A variable slit iris 510 is provided in plate 500, which variable slit iris may be expanded to different widths as set for in FIG. 10A. Similarly, in FIG. 10B, variable square iris 520 is provided, and in FIG. 10C, variable circular iris 530 is provided. It is understood that the iris may be any shape or configuration, and that the invention is not limited to the illustrative shapes of FIG. 10.

That portion of illuminating beam 100 exiting the illumination aperture 30 intersects partial beam splitter 50, with a portion of illuminating beam 100 reflected by beam splitter 50 to form beam 110, and the remainder traversing the beam splitter 50 as beam 105. Beam splitter 50 may be any optical or optical-containing component that splits illuminating beam 100 into at least two components. Such components may split beam 100 at a 90° angle, as depicted in FIG. 1, or at any other angle consonant with the function of the device of FIG. 1. Beam splitter 50 may conventionally be a semi-transparent reflecting mirror, a cube beam splitter, a polarizing cube beam splitter, or any other component or components performing the function of a beam splitter.

Reflected beam 110 is focused by lens 60, which may be a focusing lens system, such as a lens objective system, comprising two or more individual lenses or other optical components. Lens 60 creates a range of incident angles on specimen surface 95, the incident angles determined by illumination aperture 30, the distance of specimen surface 95 from lens 60, the spectral content of beam 110, and the optical properties of lens 60. In general, the specimen surface 95, which may be, for example, a diffraction grating on a wafer, is mounted on holder 90, and will scatter the light comprising beam 100 diffusely. That portion of the scattered light within the numerical aperture of lens 60 travels through lens 60 and forms a column of scattered light as scattered beam 120. The relationship between the distance of any given ray from the optical axis of lens 60 and the angle at which such ray was scattered from surface 95 can be accurately estimated from knowledge of the optical properties of the device of FIG. 1.

Beam 120 passes through beam splitter 50 and partially passes through observation aperture 40, which observation aperture 40 may be controlled as to size or shape, or both. In one embodiment, observation aperture 40 includes an iris, such as depicted in FIG. 10, and discussed above with respect to illumination aperture 30. By adjusting observation aperture 40 diameter, or more generally its shape or size, detection system 70 receives scattered rays forming a part of beam 120 which correspond to a particular range of scattered angles. Similarly, adjusting illumination aperture 30 changes the range of angles that are incident on specimen surface 95.

Detection system 70 may include any detector device for detecting any parameter associated with light forming beam 120, and thereby characterizing the received light. This may include, for example, intensity, polarization state, spectroscopic properties, or the like. In one embodiment, detection system 70 includes one or more photodiodes, photomultipliers or other elements appropriate for detecting the wavelength or the intensity, or both, of the light forming beam 120. A single element detector provides an integrated measure of the range of angles incident on specimen surface 95 as a result of change in the numerical aperture of observation aperture 40 or illumination aperture 30 or both. If wavelength dependence of the scattering properties is to be examined, light source 20 may provide different wavelengths of light in sequence over the course of measurements, or light source 20 may provide white light or short, typically femtosecond to picosecond range, laser pulses. Detection system 70 may thus include, as appropriate to the property to be examined and the form of light employed, a spectrally resolving system, such as a diffraction grating monochromator, a tunable Fabry-Perot resonator, a prism, or any of a number of standard spectroscopic tools. In one embodiment, detection system 70 permits measurements over a broad range or set of wavelengths in parallel, which is particularly advantageous where the specimen samples have negligible non-linear properties, since each component of the illumination spectrum is thus effectively independent. In another embodiment, detection system 70 includes a beam concentrator or other focusing elements to concentrate all light within the subtended range of angles of observation aperture 40, if provided, onto the detector element or elements. Detection system 70 can further include, as a component part thereof or as a separate part, various data processing components, which may optionally include a computer, such as a processor, data storage means and data retrieval means. The computer or processor components of detection system 70, or separate components, can thus provide for recording data, selectively recalling data, data analysis, generation of a model system, comparison to the model and the like.

The device of FIG. 1 further optionally includes detection system 80, which detection system 80 may be the same as or different from detection system 70. Detection system 80 includes any detector device for detecting any parameter associated with light forming beam 105, and preferably includes a photodetector for, in part, monitoring the illuminating power of beam 100, by measuring beam 105 which is a known portion of beam 105, thereby providing one or more data sets for use in calibration of the device of FIG. 1. In one embodiment, detection system 80 includes a detector array. The detection system 80 may thus include either a one-dimensional and preferably a two-dimensional detector array. Such array may include photodiodes, charge-coupled devices or other detector arrays, appropriate for the wavelength and intensities to be detected. Use of a detector array provides measurement of beam 105 over a corresponding range of incident angles. Similarly, any other desired parameter may be determined, and employed as calibration data, including use in any of a variety of statistical analysis techniques.

Although the device shown in the schematic of FIG. 1 illustrates the illumination of only a single point on specimen surface 95, a device of this invention may contain imaging optics to match the illuminated area and the observation entrance window to the lateral dimensions of the sample. Thus the area on specimen surface 95 that is analyzed is determined, in part, by the wavelength of light employed and the size of structures forming a part of specimen surface 95.

Figure 2:
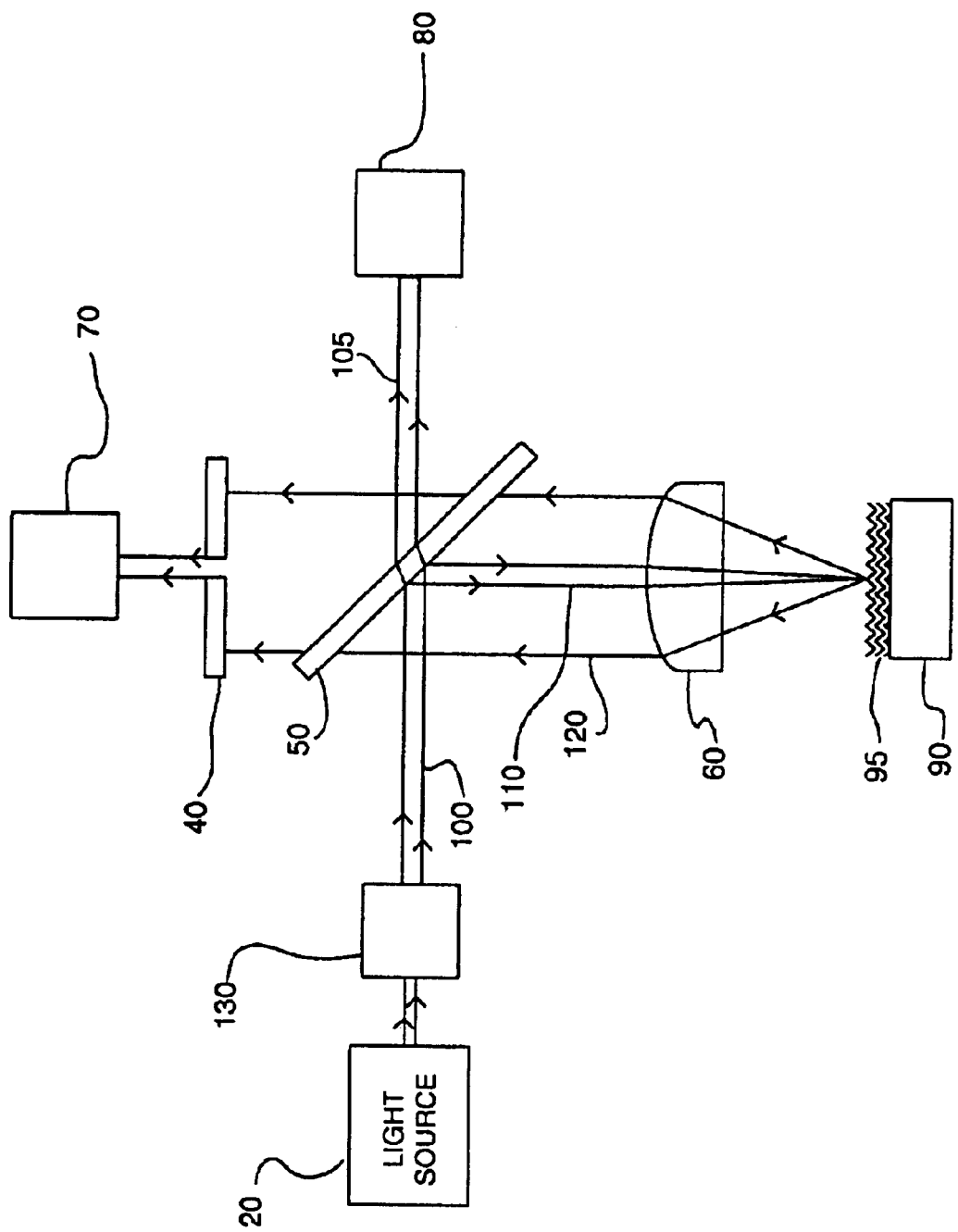
FIG. 2 is a schematic diagram illustrating an embodiment of the invention wherein a variable illumination numerical aperture is provided by means of a beam expander.

The device of FIG. 2 provides an alternative embodiment wherein illumination numerical aperture component 130 includes an adjustable telescope, or an adjustable beam expander, which changes the diameter of the column of illuminating beam 100. Through the use of optical elements such as an adjustable telescope, zoom lens array, adjustable beam expander or the like, the effective illumination numerical aperture may be altered without changing the total illuminating power of beam 100. A typical adjustable beam expander adjusts over a limited range of about 1:1 to about 6:1, but more powerful beam expanders are known and can be constructed, including construction by combination with zoom lenses as appropriate. Other combinations and permutations are possible, such that observation aperture 40 may be employed in conjunction with an adjustable beam expander or similar optics that change the diameter of the column of scattered beam 120 subsequent to observation aperture 40 but prior to detector 70.

Figure 3:
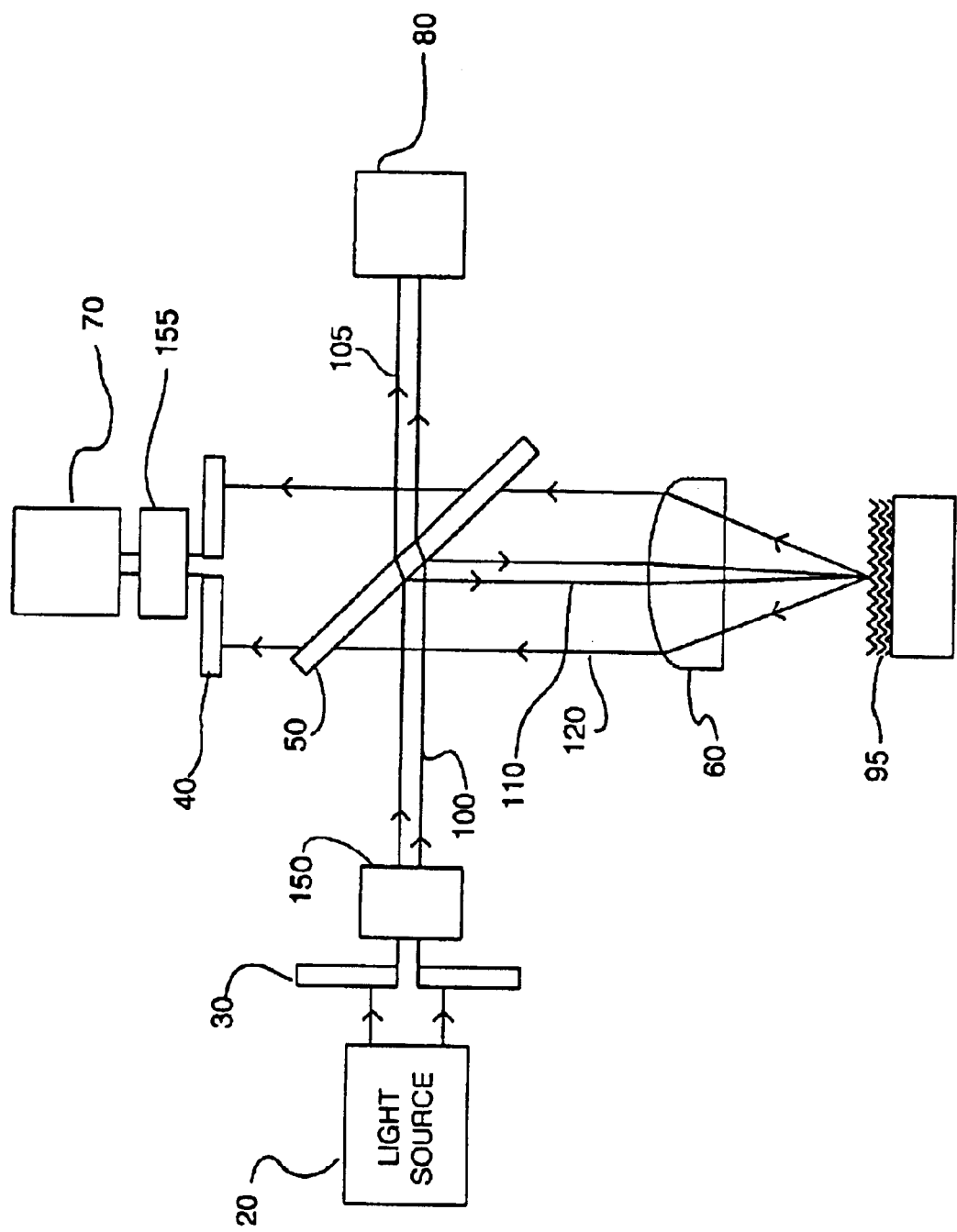
FIG. 3 is a schematic diagram illustrating an embodiment of the invention wherein both a variable illumination and observation numerical aperture is provided together with polarizing components.

FIG. 3 depicts an embodiment of this invention wherein polarizing component 150 is included, and optionally polarizing component 155. Polarizing components 150 and 155 may include a linear polarizer, a rotateable wave plate, such as a rotateable quarter-wave plate, or other polarizing optics. Polarizing components 150 and 155 may be selected so as to control the polarization state of illuminating beam 100, or of scattered beam 120, or both. In such embodiments, detector system 70, and optionally detector system 80, additionally measure one or more parameters associated with the polarization state of the light forming beam 120. It is to be understood that the arrangement of components may be altered within the scope of the invention. For example, polarizing component 150 may form a part of light source 20, and may thus be before or after illumination aperture 30. Similarly, polarizing component 155 may be before or after observation aperture 40. So too polarizing component 150 may be employed with illumination numerical aperture component 130, and may form a part thereof, or may be a separate component, and may be either before or after component 130. In any such embodiments employing polarizing optics, standard ellipsometric analytical methodologies can optionally be extended to account for possible variation in the ellipsometric state of the scattered field with distance from the optical axis, thereby providing an accurate model of the effect of these components on the measurement system.

Figure 4:
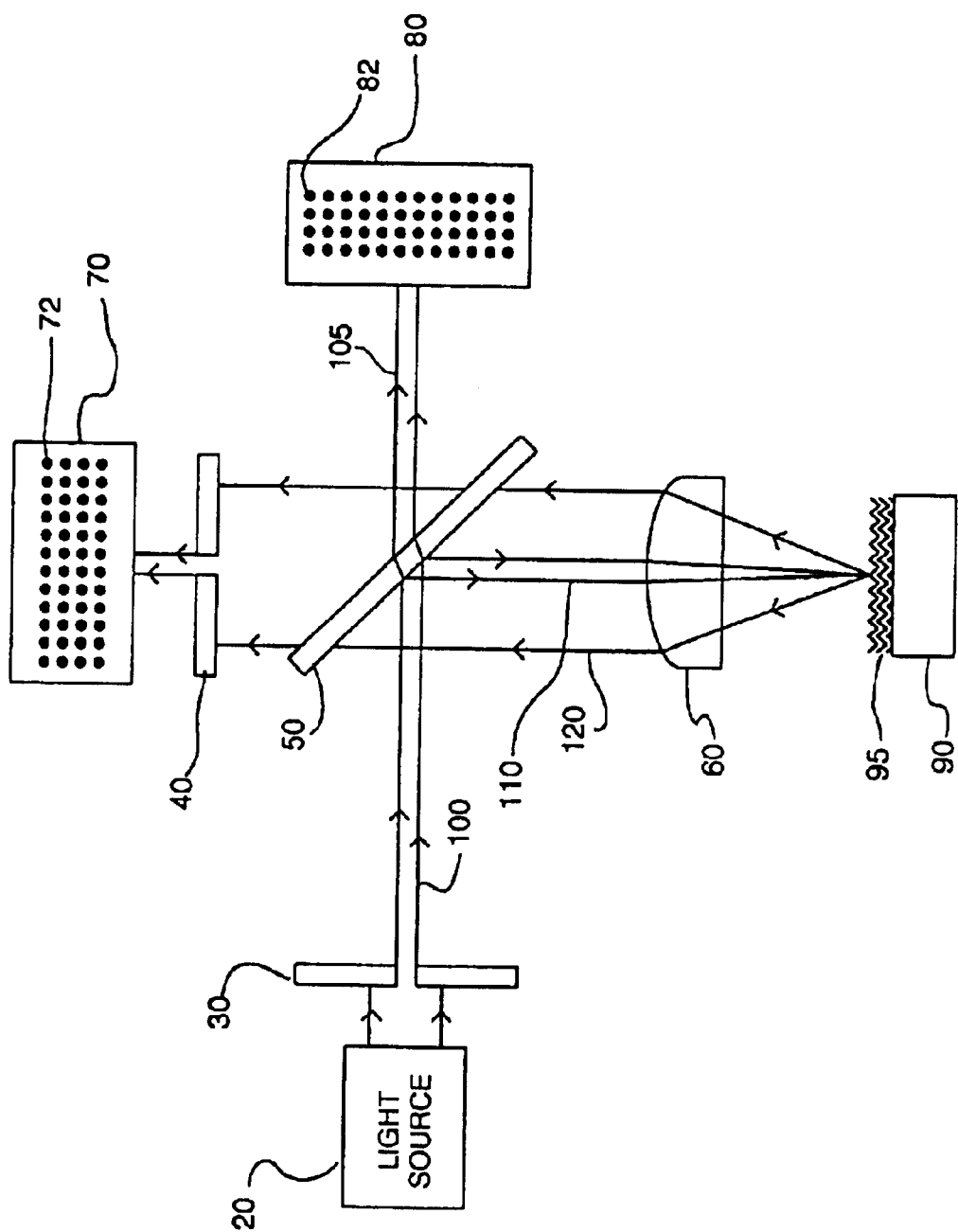
FIG. 4 is a schematic diagram illustrating an embodiment of the invention wherein a detector array is provided.

In FIG. 4 a device of an alternative embodiment is provided, wherein detection system 70 includes a plurality of detectors 72 forming a detector array. The detection system 70 may thus include either a one-dimensional (e.g., a single row or single column of detectors) and preferably a two-dimensional detector array. Such array may include photodiodes, charge-coupled devices or other detector arrays, appropriate for the wavelength and intensities to be detected. Use of a detector array provides measurement over a range of scattered angles. The detectors 72 may further include any device including a detection element that provides spatially resolved intensity measurements, such as a videcon, nuvecon or the like. While the device of FIG. 4*t* includes an observation aperture 40, it is to be appreciated that a plurality of detectors 72 forming a detector array may be employed without an observation aperture 40, or alternatively may be employed with an observation numerical aperture component 140. So too the polarizing optic elements of FIG. 3 may be employed with the array of FIG. 4. FIG. 4 further depicts detection system 80 including a plurality of detectors 82 forming a detector array, which array may be as described for detectors 72. The array of detectors 82 may be employed with any embodiment of the invention, and is not limited to the embodiment of FIG. 4.

Figure 5:
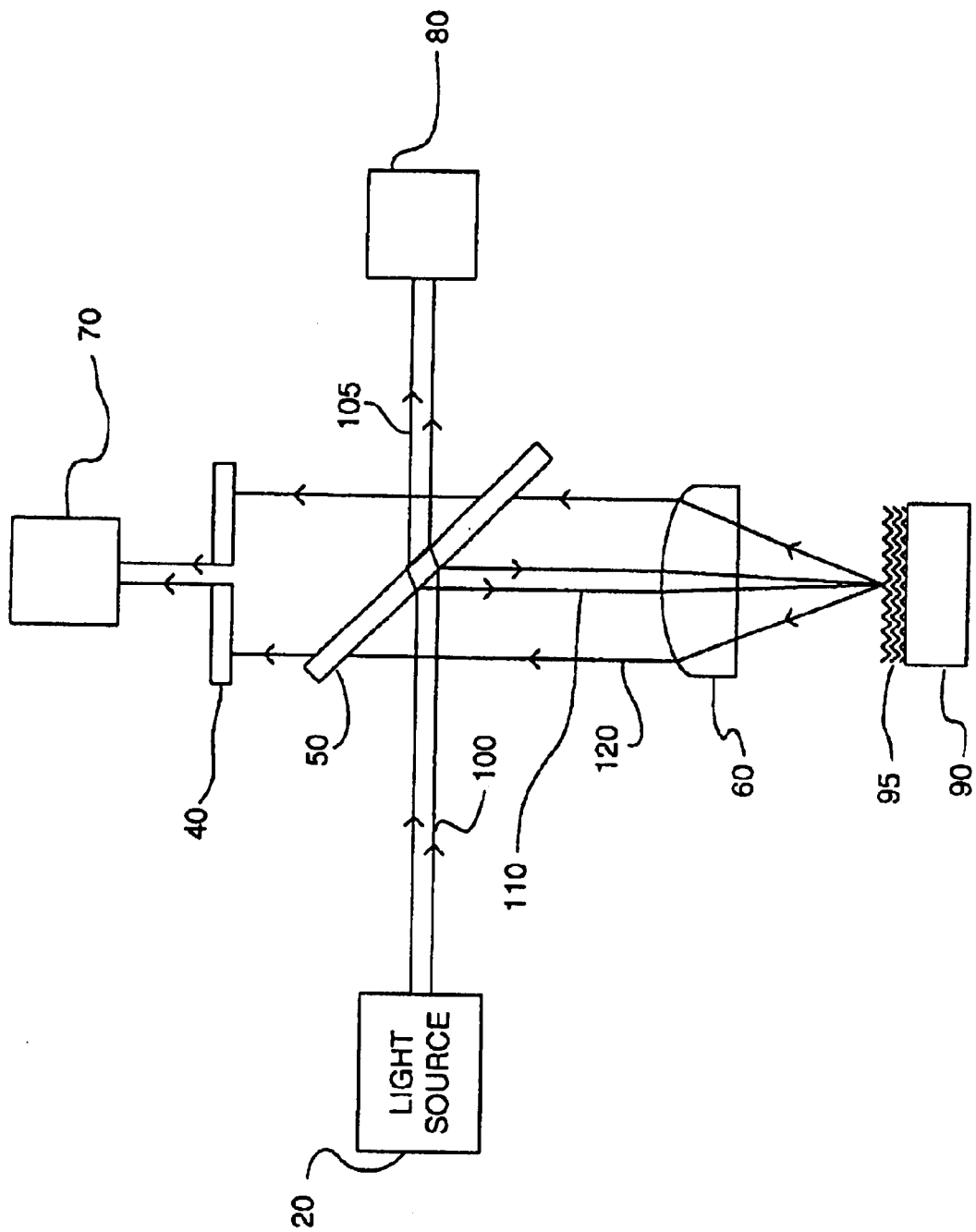
FIG. 5 is a schematic diagram illustrating an embodiment of the invention wherein a variable observation numerical aperture is provided by means of a variable iris, with a fixed illumination iris.
Figure 6:
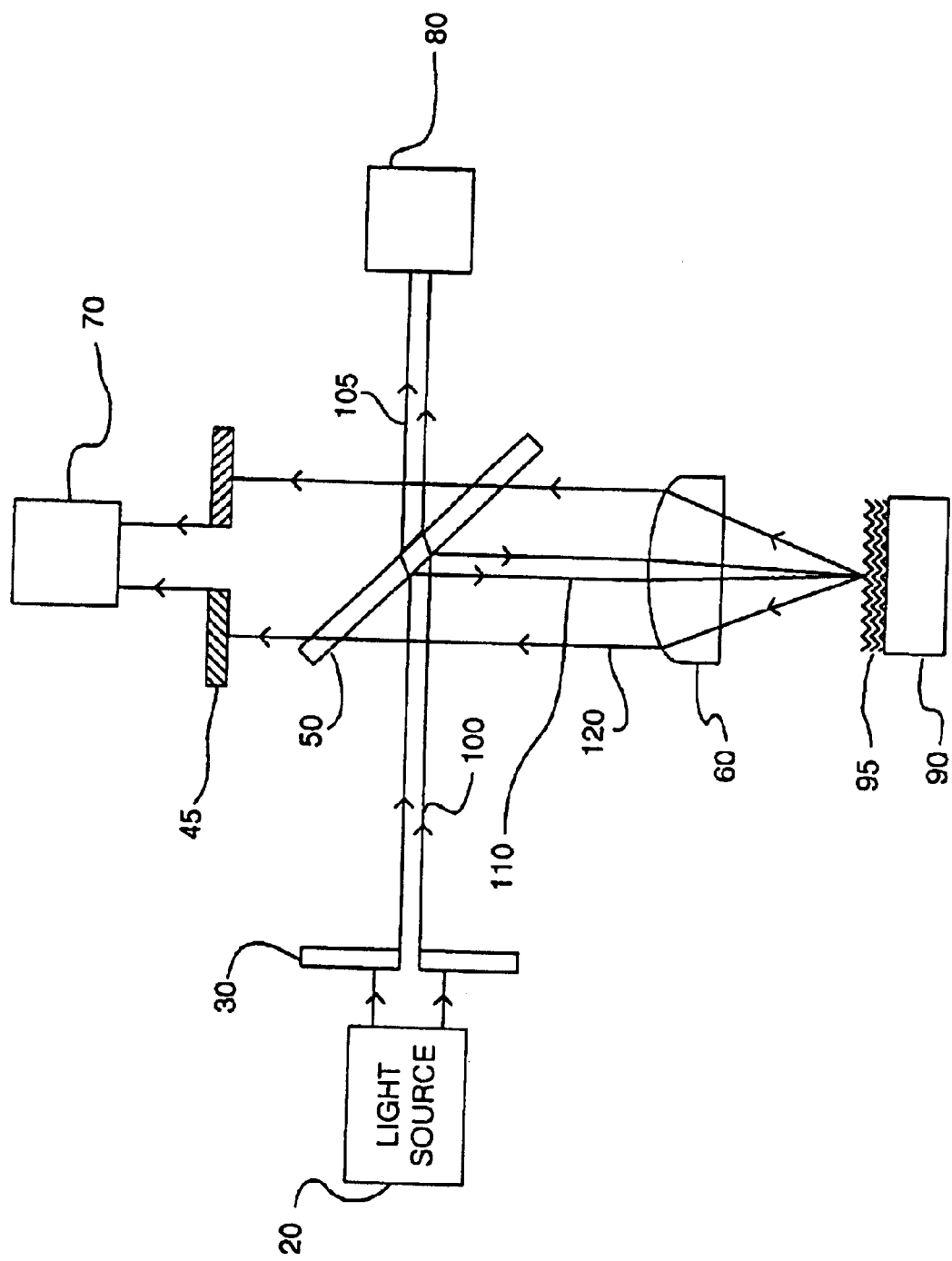
FIG. 6 is a schematic diagram illustrating an embodiment of the invention wherein a variable illumination numerical aperture is provided by means of a variable iris, with a fixed observation iris.

FIG. 5 provides an alternative embodiment device, wherein a variable illumination aperture or functionally similar illumination numerical aperture component is not provided, and wherein the only variable aperture is observation aperture 40. This embodiment may be employed for characterizing surfaces that scatter diffusely, but is in general not well suited to surfaces that are nearly specular, such as sub-wavelength diffraction gratings. A complementary alternative embodiment device is depicted in FIG. 6, wherein variable illumination aperture 30 is provided with fixed observation aperture 45. In this case, all of the scatter light within the numerical aperture of lens 60 and fixed observation aperture 45 is always observed, with the range of illuminating angles varied by means of illumination aperture 30. This embodiment may be employed with weak, diffusely-scattering surfaces, where scattering efficiency varies strongly with incident angles. Observing a large range, including but not limited to the full range, of scattered angles increases the signal level over that obtainable for a limited observation numerical aperture.

In addition, the numerical aperture may be changed or effected by imaging techniques rather than by directly adjusting the aperture stops. For many applications, use of imaging techniques provides superior results. For example, use of an iris, particularly for the illumination aperture, may result in diffraction rings as a result of the passage of light through the iris. Thus a pinhole aperture may result in an Airy disk, with concentric circles representing diffraction orders. System design may account for diffraction by imaging the illumination iris onto the aperture stop of lens 60, particularly where lens 60 includes an objective lens systems, such as a focusing lens system including two or more individual lenses and an aperture stop. The imaging system employed will typically include one or more lenses, in addition to the lenses illustrated in the figures, and may further include other optical elements known in the art. The imaging system employed may also magnify or reduce the illumination iris, and thereby effect a change in the numerical aperture.

It thus follows that there are several techniques that can be employed to adjust the numerical aperture, including but not limited to (a) a zoom element that may be employed to extend or retract the effective focal length of the objective, thereby decreasing or increasing the numerical aperture; (b) adjusting the effective size of the aperture stop (which determines the diameter of the relevant light cone) by imaging the aperture stop with a variable magnification; (c) printing the aperture stops, or more particularly, the spatial Fourier Transform of the aperture stop, on a slide, or alternatively patterning the aperture stops in a spatial light modulator which is then projected into the system, whereby changing the slides or patterns changes the aperture stop; (d) directly changing the size of the aperture, such as by opening or closing an iris; and (e) a combination or permutation of any or some of the foregoing. It is also possible and contemplated that the numerical aperture may be changed by means of liquid crystal components, such that the liquid crystals act as a switch or cell that either blocks or transmits light, thereby forming a part of the aperture. Use of liquid crystal arrays or panels can further provide a polarizer function. The use of liquid crystal arrays or panels thus can form a part of a variable numerical aperture component, such that a device of this invention has no moving mechanical parts. All of the foregoing are intended to be included in the disclosure of a numerical aperture herein, and in the figures and described devices any of the foregoing methods of changing the numerical aperture may be substituted.

FIG. 8A provides an alternative embodiment device, utilized as hereafter described to demonstrate that the differential numerical aperture (DNA) signature distinguishes between different diffraction grating samples. Light 300 from light source 220, such as a Helium-Neon laser, reflects from partial beam splitter 240 forming beam 310, which beam passes through polarizer 250, such as a Glan-Thomson polarizer, which polarizes the beam along the grooves on diffraction grating specimen 295 on base 290. The diameter of beam 310 expands by a factor of six as it traverses a Newtonian telescope comprising lens 280 and lens 285, such that the resulting beam 320 becomes large enough to fill the aperture of microscope objective 260. Panel 230 with a narrow rectangular slit is positioned between the telescope comprising lens 280 and lens 285 and microscope objective 260, and forms beam 320 into a thin rectangular beam 330 the position of which moves along its long axis as the dial of a micrometer pushes panel 230. Slit 235, as shown in FIG. 8B, is oriented lengthwise along the grooves on diffraction grating specimen 295. In one embodiment, slit 235 is approximately 500 μm wide and at least as long as the aperture of microscope objective 260. Microscope objective 260 focuses rectangular beam 330 onto specimen 295 and collimates reflected beam 340. The portion of reflected beam 340 which passes slit 235 on its return path is again polarized by polarizer 250, passes through beam splitter 240, passes through spectral filter 275, which removes background light, and then excites photodetector 270. The DNA signature is photodetector 270 response as a function of slit 235 position.

In the embodiment of FIG. 8, the slit 235 is placed after beam splitter 240 and in close proximity to objective 260. This minimizes the effect of diffraction from slit 235, which in general reduces the crispness with which the range of illuminating angles is defined. An alternative embodiment retains an illumination aperture in the position as shown by the device of FIG. 1, before the beam splitter, and additionally includes an imaging system to relay an image of the illumination aperture into the aperture stop of microscope objective 260.

The devices of this invention generally provide illumination of known intensity as a function of incident direction, and optionally wavelength and polarization state, and provide for the observation of light scattered by the observed surface into a particular direction and optionally polarization state. The efficiency of observation may vary in a known manner. The surface model, in general referred to here as a BRDF, provides the probability that a light ray at a given wavelength incident from a given direction with a given polarization state will be scattered into a particular direction and polarization state. The scattering probabilities depend on the sample's surface parameters, and it is these parameters that the devices and methods of the invention determine. By convoluting the BRDF and illumination function over the range of illumination states, it is possible to construct the intensity of light scattered into a particular direction and polarization state. The scattered intensity and the observation efficiency is then convoluted over the range of observation states. By comparing the result of this convolution with the measured DNA datum for that combination of illumination state, observation state and surface parameters, an error between the simulation and the measurement is determined. The illumination or observation state, or both, are then differentially changed, thereby producing a new datum and error point. This process is repeated until a desired number of points have been measured. Utilizing the measured data, the surface parameters can be varied, and the simulation and error metric recomputed, until a set of surface parameters that result in the lowest error is determined. The set of surface parameters having thus been found within the accuracy of the model, technique, and experimental error, the analysis is complete.

The methods and devices of this invention thus provide for determining data points for a given specimen over a range of either illumination or observation numerical apertures, or both, which range of numerical apertures necessarily subtends a range of incident and/or scatter angles. It is understood that the data points may be step-wise or over time. For example, the numerical aperture of the illumination numerical aperture component may incrementally increase or decrease, at any desired rate, over a range from 0 to about 1. At each incremental step, the scattered light intensity, over the range of angles detected, is measured. This data may then be accumulated in stepwise fashion. Alternatively, the numerical aperture may vary at a known rate over time, with detection of scattered light intensity correlated to the initial numerical aperture and the rate of variation. Similarly the observation numerical aperture may optionally be varied in incremental steps or at a known rate, and correlated to the detection of scattered light intensity. By this means, the incident angle and the detected scatter angle may be varied, with this variation thereby providing the basis for analysis, including determination of BRDF.

In general, the DNA method of this invention is suited to finding the unknown parameters of a surface scattering model. Since the DNA signature is a convolution of the model surface scattering function and the illumination and observation numerical aperture functions, the scattering function itself cannot in general be directly deduced. However, if changes in surface parameters result in a change in scattering behavior at any observed angle, such changes will be represented in the DNA signature. If the change in surface parameters increases scattering over a broad range of observation angles, the effect on the DNA signature will be large because of the integrated nature of the measurement. However, if the change in surface parameter results in a change over only a very small range of observation angles, the effect on the DNA signature will be comparatively smaller.

In CD scatterometry, it is typical for the sample to be a diffraction grating whose period is sub-wavelength, resulting in a BRDF which changes slowly over a large range of observation angles. The DNA method of this invention is well suited to such measurements since even small changes in reflectance over a broad range of angles produces a sizeable effect on the DNA signature. The DNA method is not, in general, as well suited for samples that vary rapidly with observation angle, since the integrating nature of the technique tends to "average" over the peaks and valleys. There are, however, exceptions to this general statement; for example, the observation of changes in surface parameters that result in a scaling of the sample's BRDF, since in this instance the integrated effect will still be large.

The invention thus provides a method which measures scattering as a function of angle-of-incidence by differentially changing the illumination or observation numerical apertures, or both, as opposed to the known and conventional method of laterally scanning across an entrance pupil. The method and devices of this invention may thus be used for performing angle-resolved scatterometry, ellipsometry, and bi-directional reflectance distribution function measurement at a single wavelength or spectroscopically.

The methods and device of this invention may also be adapted to transmission studies. In the case of bi-directional transmission distribution function measurement the illumination is placed underneath the sample.

The observation and illumination apertures can be independently controlled as to numerical aperture, and may additionally be varied in position relative to the beam, size or in shape, or a combination thereof. For example, varying a fixed aperture relative to the beam may, depending on the configuration, result in an effective variation in the numerical aperture.

Figure 7:
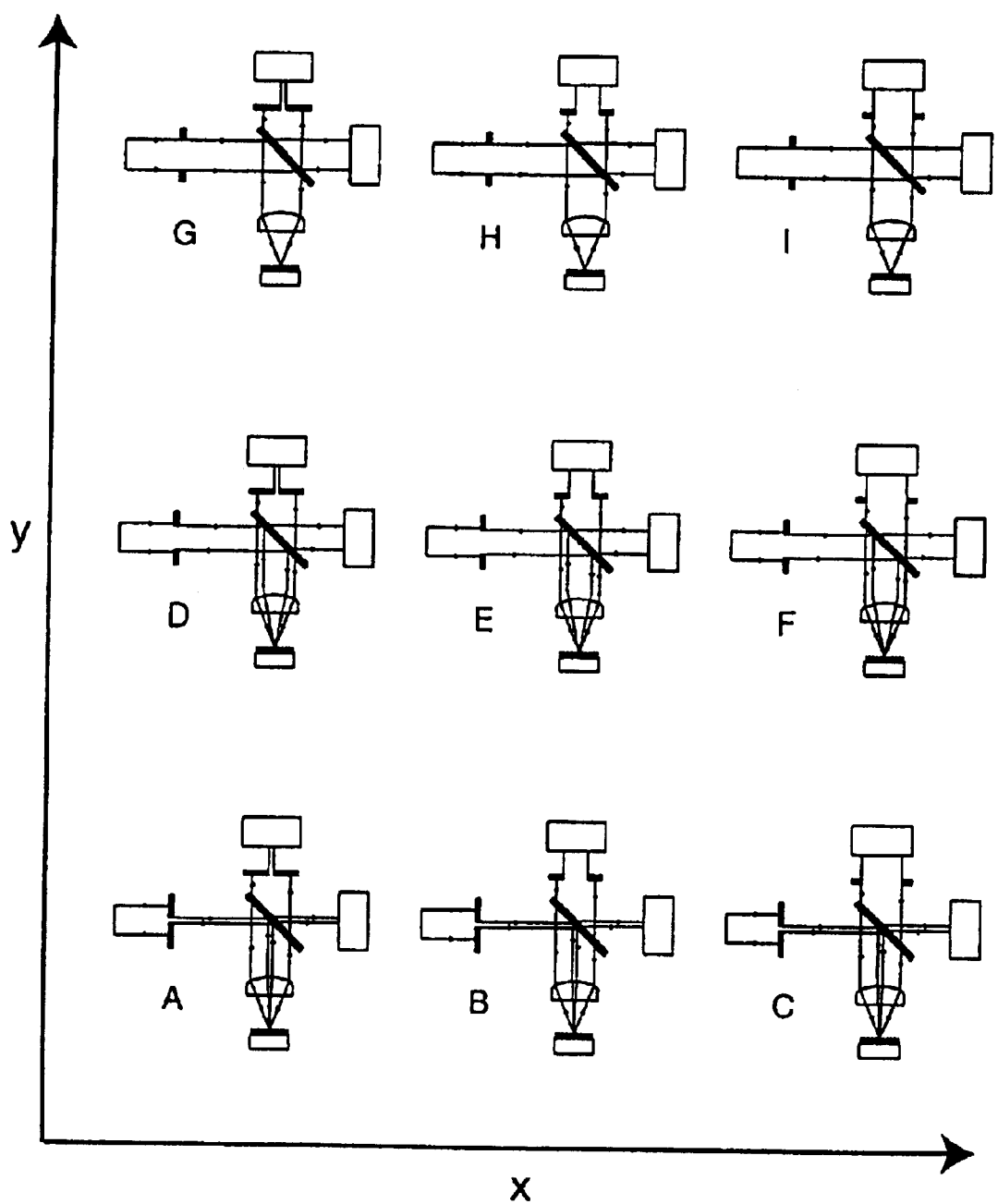
FIG. 7 is a schematic diagram showing ranges of variation in numerical aperture at different observation points, with corresponding detection of different incident and reflective angles, utilizing an embodiment of the invention wherein both a variable illumination and observation numerical aperture is provided.

FIG. 7 illustrates simplified generic conceptual measurement sequences, utilizing a device of FIG. 1. At each setting of the illumination numerical aperture, the photocurrent at the detectors is measured as a function of the observation numerical aperture. The incremental difference in photocurrent determines the contribution from higher-angle scattering. In FIG. 7, the setting at A depicts both the illumination and observation aperture stops almost completely closed, so that the numerical apertures for both is at a low number, such that the sample is illuminated solely at near-normal incidence and only specular reflection is measured. In the settings shown at B and C (moving along the X axis), the observation aperture stop is opened in incremental steps, with an increasing numerical aperture value for the observation numerical aperture component, with the observation photocurrent recorded at each steps. Only two steps, B and C, are shown, it being understood that a multitude of steps, and of much finer or small increment than depicted, may be employed. In the settings shown at D to F, the illumination aperture stop is opened one increment and held at that position, while the observation aperture stop is opened in small steps. The difference between the measurements resulting from the positions at D to F and the counterpart measurements resulting from the positions at A to C is the contribution of scattering from off-axis illumination. In the settings shown at G to I, a final set of measurements is made with the illumination numerical aperture at its largest setting while the observation aperture stop is opened in small steps. It is also possible to move along the Y axis, such as from A to D to G, so that the observation aperture stop is fixed and the illumination observation aperture stop is opened in small steps.

The general sequence as described in FIG. 7 contains, within the limits of the highest and lowest numerical aperture settings and the bandwidth of the detectors, all of the scattering information from samples having axial symmetry. For samples not having axial symmetry, the shape of the illumination and observation apertures is matched to provide the appropriate symmetry and the measurement sequence modified accordingly. For the case of diffraction gratings, the apertures may have rectangular symmetry, and the measurement sequence may proceed along the diagonal of illustrated settings of FIG. 7.

Figure 9:
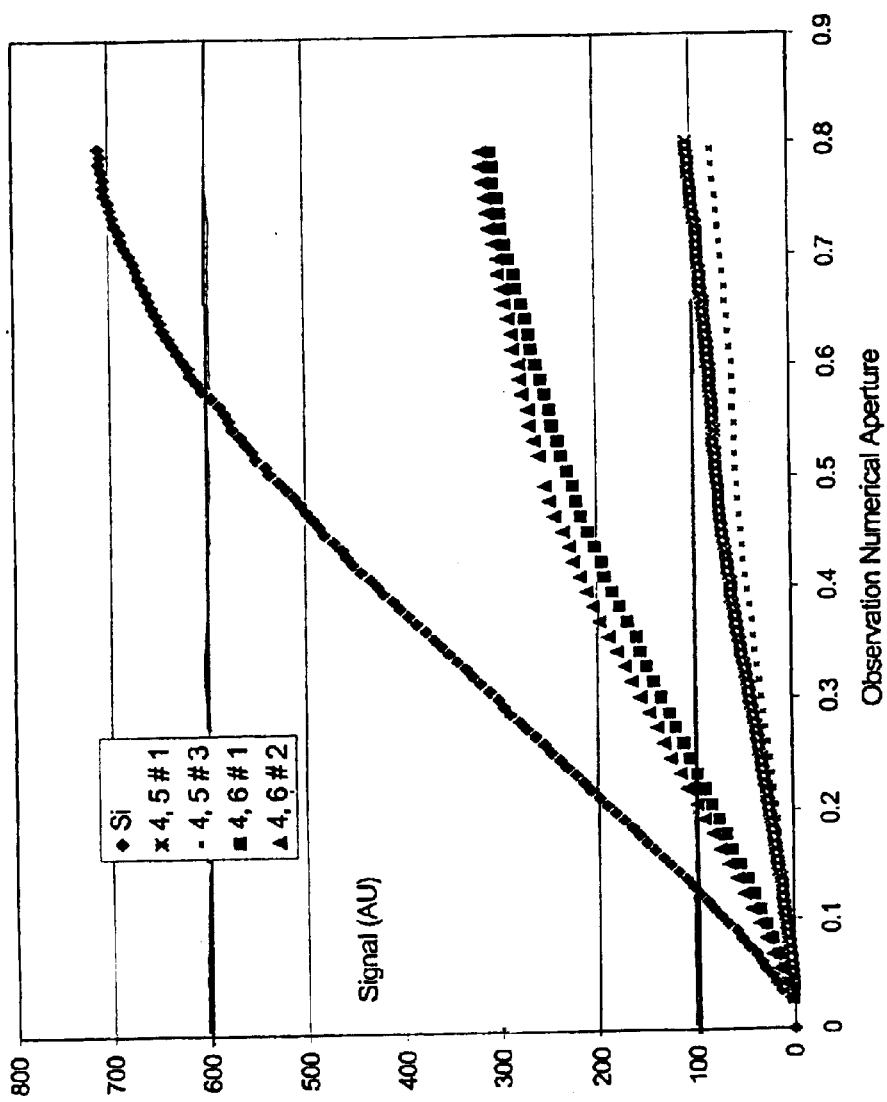
FIG. 9 is a graph of the signal as a function of observation numerical aperture obtained from three specimens using a differential numerical aperture device of this invention wherein a single polarizer and single variable numerical aperture is employed for both illumination and observation; and, FIG. 10 is a schematic diagram of variable irises that may be employed in embodiment of the invention.

Utilizing a device as shown generally in FIG. 8, measurements were performed on both a clean bare silicon wafer and on diffraction gratings, made by photolithographic means, contained at row 4, columns 5 and 6, of a wafer, such as a 300 mm silicon wafer. The panel 230 was moved by a micrometer. Initially the micrometer dial was set so that the lower edge of slit 235 was on the optical axis; the reflected beam was thus completely blocked by slit 235 on its return path and zero signal obtained. By means of the micrometer the lower edge of the slit was moved below the optical axis in 2.5 µm steps, with the reflected power measured by photodetector 270. This differential process was continued until the reflected power stopped increasing, signifying that that the slit was centered on the optical axis. The diffraction gratings were then measured by similar means, with the grating at row 4, column 5 measured in steps of 2.5 µm, steps of 5.0 µm, and steps of 5.0 µm. The neighboring grate at row 4, column 6 was measured twice, each time in steps of 5.0 µm. The resulting data is shown in FIG. 9, wherein the signal is shown on the Y axis, and the observation numerical aperture, calculated as set forth below, shown along the X axis. The signature from the bare silicon wafer is "Si", "4,5 #1" is the measure of the grating at row 4, column 5, in steps of 2.5 µm, while "4,5 #3" is the same grating measured in steps of 5.0 µm. The signatures for "4,6 #1" and "4,6 #2" are both for the grating at row 4, column 6, both measured in steps of 5.0 µm.

The data of FIG. 9 shows that the signatures of the two gratings are well separated compared to the repeatability of an individual signature, and are also well separated from bare silicon. The signatures increase monotonically with observation numerical aperture because the sample is specular and the illumination numerical aperture exceeds the observation numerical aperture for all data presented. The micrometer readings were converted to an observation numerical aperture value by using the sine law for an ideal lens illuminated by collimated rays, and the known 0.8 objective numerical aperture of the objective 260. The sine law is $$\sin \Theta = x/f \qquad \text{EQ. 1}$$

where x is the distance of the ray from the optical axis, f is the focal length of the objective, and $\Theta$ is the angle which the ray makes with optical axis after exiting the objective. A ray initially parallel to the optical axis at a height x above it will strike the sample at angle $\Theta$. The position of the lower edge of the slit below the optical axis, given the specular nature of the sample, determines the effective observation system numerical aperture, defined for a sample in air as $$NA = \sin \Theta = x/f \qquad \text{EQ. 2}$$

where x now represents the distance that the lower edge of the slit is below the optical axis, and NA is the numerical aperture. Initially the observation numerical aperture is zero. As the lower edge of the slit moves below the optical axis the observation numerical aperture increases until it reaches the maximum value set by the microscope objective 260, which is a known quantity, 0.8, such that $$0.8 = x\_max/f \qquad \text{EQ. 3}$$

The value for x_max was determined to be 2.97 mm by subtracting the micrometer reading at the lowest position of zero signal from the micrometer reading at the position of maximum signal. Eliminating f, the numerical aperture is obtained as a function of x $$NA = 0.8 \cdot x/x\_max \qquad \text{EQ. 4}$$

The calculated value for NA was thus plotted against signal as shown in FIG. 9.

In the foregoing example, the illumination consisted of a single wavelength and polarization state. With the slit oriented along the grooves of the grating sample, it was appropriate to consider a model in which the sample acts as a simple mirror whose reflectance changes with angle. For simplicity, the slit is considered to be sufficiently such narrow that the sample's effective reflectance did not change appreciably over incident directions orthogonal to the length of the slit. Although the Gaussian nature of a laser beam does not produce a uniform illumination over the area of the slit, this can be approximated as uniform illumination for the sake of simplicity. Within this model, then, no signal is seen in the initial state of the measurement since in the model the grating acts as a simple mirror with an effective reflectance; with the specular model it is predicted that none of the illuminating light can be observed within the observation numerical aperture defined by the slit. As the slit is lowered below the optical axis it is predicted that illumination which is as far from the optical axis, whether above or below, as the lower edge of the slit is below the axis will fall within the observation numerical aperture and be measured. In the first few measurements, as shown in FIG. 9, the lower edge of the slit is just barely below the optical axis so that only the sample's effective reflectance at normal incidence is important. This first measurement constitutes an uncalibrated measure of the sample's surface-normal reflectivity. Given that the reflectance of the silicon sample is known, it is possible to directly calibrate measurement of the grating samples for near-normal incidence.

As the slit is differentially lowered, if the grating's effective reflectance were constant the signal level would increase linearly at twice the rate at which the slit is lowered, the factor of two resulting from the portion of the slit above the axis remaining fully illuminated, the portion below the slit increasing linearly as the slit is lowered, with both the portion above and below the slit observed by the system. Inspection of the measurement signatures shows that to first order the signatures are linear in observation numerical aperture. As the slit is lowered, the observation system continues to accumulate signal over larger and larger angles of incidence until finally the limit of the objective is reached. Only the initial measurements when the slit is just below the axis have an obvious interpretation; in general, the measurement represents the sample's reflectance integrated over a range of angles. Using the analysis procedure described above, however, best-fit surface parameters can be found.

Utilizing the foregoing, a device for DNA analysis can be constructed that is compact and may be implemented in a variety of configurations. Such configurations may include application as a module or component of an integrated processing and manufacturing device for semiconductor manufacture. For example, the device of FIG. 8 incorporates a single movable piece, panel 230 including slit 235, which functions simultaneously as both the observation and illumination numerical aperture. By utilizing a diode laser for light source 220, and a polarizing cube beam splitter for beam splitter 240 and polarizer 250, the assembly of the device can fit within dimensions on the order of approximately 5 cm by 5 cm by 25 cm or smaller. Similarly, the devices of FIG. 1 and similar embodiments can employ as few as one or two moving parts, and can fit within dimensions on the order of approximately 5 cm by 20 cm by 20 cm or smaller. Utilizing a liquid crystal aperture, it is possible to provide a device of this invention with no moving mechanical parts. Effective miniaturization is thus both possible and contemplated, and is desired for many applications.

The preceding examples can be repeated with similar success by substituting the generically or specifically described components and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for determining parameters of a sample comprising:
    a source for generating a beam of light;
    a variable illumination numerical aperture component, variable over a numerical aperture range while obtaining data for determining parameters, the varying numerical aperture thereby varying the range of angles at which illuminating rays strike the sample;
    a variable observation numerical aperture component, variable over a numerical aperture range while obtaining data for determining parameters, the varying numerical aperture thereby varying the range of angles at which scattered rays from the sample are accepted; and
    a first detection system positioned to receive and characterize the light accepted by the variable observation numerical aperture component.

2. The apparatus of claim 1, further comprising a beam splitter positioned to direct the beam of light generated by the source to the sample.

3. The apparatus of claim 1, further comprising a lens positioned such that the lens focuses the illuminating rays striking the sample and collects scattered rays from the sample.

4. The apparatus of claim 1, further comprising:
    a first component for polarizing light positioned such that the component polarizes light striking the sample; and
    a second component for polarizing light positioned such that the component polarizes light scattered from the sample prior to receipt and characterization by the first detection system.

5. The apparatus of claim 4, wherein the first component for polarizing light and the second component for polarizing light comprise elements selected from the group consisting of a polarizer, a wave plate, an electrooptic modulator, a photoelastic modulator and a liquid crystal.

6. The apparatus of claim 1, further comprising a second detection system positioned to receive and characterize a first portion of the light subsequent to the variable illumination numerical aperture but prior to striking the sample.

7. The apparatus of claim 6, further comprising a beam splitter positioned to direct the first portion of the light to the second detection system and a second portion of the light to the sample.

8. The apparatus of claim 1, wherein the variable illumination numerical aperture comprises a member selected from the group consisting of an aperture with an iris, a zoom lens assembly, a variable beam expander, a variable aperture stop magnification imaging assembly, a spatial Fourier transform of the aperture stop assembly and a combination of the foregoing.

9. The apparatus of claim 8, wherein the iris is of any shape.

10. The apparatus of claim 1, wherein the first detection system comprises a member selected from the group consisting of a photodetector and a spectrometer.

11. The apparatus of claim 1, wherein the first detection system comprises a computer-compatible output for recording data relating to receipt and characterization of light.

12. The apparatus of claim 1, further comprising a processor for controlling the numerical aperture of the variable illumination numerical aperture component and the aperture of the variable observation numerical aperture component.

13. The apparatus of claim 1, wherein the numerical aperture of the variable illumination numerical aperture component is variable over a numerical aperture range from 0 to about 1.

14. An apparatus for determining parameters of a sample comprising:
a source for generating a beam of light;
a variable illumination numerical aperture component for varying the numerical aperture over a numerical aperture range while obtaining data for determining parameters, thereby varying the range of angles at which illuminating rays strike the sample;
an observation aperture component, accepting scattered rays from the sample at a fixed range of angles; and
a first detection system positioned to receive and characterize the light accepted by the observation aperture component.

15. The apparatus of claim 14, further comprising a beam splitter positioned to direct the beam of light generated by the source to the sample.

16. The apparatus of claim 14, wherein the first detection system comprises a detector array for detecting the light accepted by the observation aperture component over the range of angles accepted by the observation aperture component.

17. The apparatus of claim 14, further comprising:
a first component for polarizing light positioned such that the component polarizes light striking the sample; and
a second component for polarizing light positioned such that the component polarizes light scattered from the sample prior to receipt and characterization by the first detection system.

18. The apparatus of claim 17, wherein the first component for polarizing light and the second component for polarizing light comprise elements are selected from the group consisting of a polarizer and a wave plate.

19. The apparatus of claim 14, further comprising a second detection system positioned to receive and characterize a first portion of the light subsequent to the variable illumination numerical aperture component but prior to striking the sample.

20. The apparatus of claim 19, further comprising a beam splitter positioned to direct the first portion of the light to the second detection system and a second portion of the light to the sample.

21. The apparatus of claim 14, wherein the variable illumination numerical aperture component comprises a member selected from the group consisting of an aperture with an iris, a zoom lens assembly, a variable beam expander, a variable aperture stop magnification imaging assembly, a spatial Fourier transform of the aperture stop assembly and a combination of the foregoing.

22. The apparatus of claim 14, wherein the first detection system comprises a member selected from the group consisting of a photodetector and a spectrometer.

23. The apparatus of claim 14, wherein the first detection system comprises a computer-compatible output for recording data relating to receipt and characterization of light.

24. The apparatus of claim 14, further comprising a processor for controlling the numerical aperture of the variable illumination numerical aperture component.

25. An apparatus for determining parameters of a sample comprising:
a source for generating a beam of light;
an illumination aperture component, determining the range of angles at which illuminating rays strike the sample;
a variable observation numerical aperture component for varying the numerical aperture over an incremental numerical aperture range while obtaining data for determining parameters, thereby varying the range of angles at which scattered rays from the sample are accepted; and
a first detection system positioned to receive and characterize the light accepted by the variable observation aperture component.

26. The apparatus of claim 25, further comprising a beam splitter positioned to direct the beam of light generated by the source to the sample.

27. The apparatus of claim 25, further comprising a lens positioned such that the lens focuses the illuminating rays striking the sample and collects scattered rays from the sample.

28. The apparatus of claim 25, further comprising:
a first component for polarizing light positioned such that the component polarizes light striking the sample; and
a second component for polarizing light positioned such that the component polarizes light scattered from the sample prior to receipt and characterization by the first detection system.

29. The apparatus of claim 28, wherein the first component for polarizing light and the second component for polarizing light comprise elements are selected from the group consisting of a polarizer, a wave plate, an electrooptic modulator, a photoelastic modulator and a liquid crystal.

30. The apparatus of claim 25, further comprising a second detection system positioned to receive and characterize a first portion of the light subsequent to the illumination aperture component but prior to striking the sample.

31. The apparatus of claim 30, further comprising a beam splitter positioned to direct the first portion of the light to the second detection system and a second portion of the light to the sample.

32. The apparatus of claim 25, wherein the first detection system comprises a member selected from the group consisting of a photodetector and a spectrometer.

33. The apparatus of claim 25, wherein the first detection system comprises a computer-compatible output for recording data relating to receipt and characterization of light.

34. The apparatus of claim 14, further comprising a processor for controlling the numerical aperture of the variable observation numerical aperture component.

35. A method for determining parameters of a sample comprising the steps of:
generating a beam of light;
focusing the beam of light on the sample;
varying at least one parameter selected from the group consisting of the range of angles of incidence of the beam of light to the sample and the range of angles of detected scatter from the sample by means of at least one variable numerical aperture; and
detecting and characterizing the scattered light.

36. The method of claim 35, wherein the step of varying at least one parameter comprises varying both the range of angles of incidence of the beam of light to the sample and the range of angles of detected scatter from the sample.

37. The method of claim 36, where the range of angles of incidence of the beam of light to the sample is varied by means of a first variable numerical aperture and the range of angles of detected scatter from the sample is varied by means of a second variable numerical aperture.

38. The method of claim 35, further comprising the steps of:

polarizing the light striking the sample; and polarizing the light scattered from the sample.

39. The method of claim 35, wherein the at least one variable numerical aperture comprises a member selected from the group consisting of an aperture with an iris, a zoom lens assembly, a variable beam expander, a variable aperture stop magnification imaging assembly, a spatial Fourier transform of the aperture stop assembly and a combination of the foregoing.

40. The method of claim 35, wherein detecting and characterizing comprises use of a device selected from the group consisting of a photodetector and a spectrometer.

41. The method of claim 35, wherein detecting and characterizing comprises a computer-compatible output for recording data relating to receipt and characterization of light.

* * * * *